United States Patent [19]

Currier

[11] Patent Number: 5,403,314
[45] Date of Patent: Apr. 4, 1995

[54] APPARATUS FOR RETAINING SPINAL ELEMENTS IN A DESIRED SPATIAL RELATIONSHIP

[75] Inventor: Bardford L. Currier, Rochester, Minn.

[73] Assignee: AcroMed Corporation, Cleveland, Ohio

[21] Appl. No.: 14,312

[22] Filed: Feb. 5, 1993

[51] Int. Cl.$^6$ .............................................. A61B 17/56
[52] U.S. Cl. ................................ 606/61; 403/388; 403/396; 403/400
[58] Field of Search ................ 606/53, 59, 60, 61, 606/72, 73; 403/400, 398, 396, 388, 389

[56] References Cited

U.S. PATENT DOCUMENTS

| | | | |
|---|---|---|---|
| 4,111,580 | 9/1978 | Falcioni | 403/388 |
| 4,648,388 | 3/1987 | Steffee | 606/61 |
| 4,655,199 | 4/1987 | Steffee | 606/61 |
| 5,053,034 | 10/1991 | Olerud | 606/60 |
| 5,254,118 | 10/1993 | Mirkovic | 606/61 |

*Primary Examiner*—Tamara L. Graysay

*Attorney, Agent, or Firm*—Tarolli, Sundheim & Covell

[57] ABSTRACT

An apparatus for use in retaining spinal elements in a desired spatial relationship includes a fastener for engaging a spinal element. A longitudinal member is positionable along the spinal column. A connector member interconnects the fastener and the longitudinal member. The connector member has a mounting section with surface means defining a first opening through which the fastener extends. The longitudinal member extends through a second opening in the connector member. The axis of the opening through which the longitudinal member extends is perpendicular to top and bottom surfaces of the connector member. The mounting section has a side surface extending at an acute angle to the top and bottom surfaces. The connector member includes a surface that is parallel to the longitudinal axis of the opening through which the longitudinal member extends. The side surface of the mounting section extends at an acute angle to the surface of the connector member which is parallel to the longitudinal axis of the opening through which the longitudinal member extends.

6 Claims, 4 Drawing Sheets

APPARATUS FOR RETAINING SPINAL ELEMENTS IN A DESIRED SPATIAL RELATIONSHIP

BACKGROUND OF THE INVENTION

The present invention relates to an apparatus which is used to retain spinal elements, such as vertebrae, in a desired spatial relationship.

A known apparatus for retaining vertebrae in a desired spatial relationship is disclosed in U.S. Pat. No. 4,648,388. The apparatus includes a plurality of threaded fasteners which are connected with vertebrae of a human spinal column. Retaining rods are bent to a configuration which is a function of the desired spatial relationship between vertebrae of the spinal column. After a rod has been bent to the desired configuration, it is inserted into clamps connected with the fasteners. The clamps are then engaged to hold the vertebrae against movement relative to the rod. Other known apparatus for retaining vertebrae in a desired spatial relationship are disclosed in U.S. Pat. Nos. 4,611,581; 4,655,199; and 4,887,595.

The prior art devices are difficult to use for retaining cervical vertebrae of the spinal column in a desired spatial relationship. Due to the structure of the cervical vertebrae, fasteners must extend into the cervical vertebrae and relative to the rod in directions that the prior art devices do not readily permit.

SUMMARY OF THE INVENTION

The present invention provides an apparatus for use in retaining spinal elements, such as vertebrae, in a desired spatial relationship. More specifically, the apparatus is for retaining cervical vertebrae of the spinal column in a desired spatial relationship. The apparatus includes a fastener for engaging a spinal element. A longitudinal member, such as a rod, is positionable along the spinal column. A connector member interconnects the fastener and the longitudinal member.

The connector member has a mounting section with surface means defining a first opening through which the fastener extends. The connector member also includes surface means defining a second opening through which the longitudinal member extends. The connector member has top and bottom surfaces when connected to the spinal column. The axis of the opening through which the longitudinal member extends is perpendicular to the top and bottom surfaces. A side surface of the mounting section extends at an acute angle to the top and bottom surfaces. The side surface of the mounting section also extends at an acute angle to a surface of the connector member which is parallel to the longitudinal axis of the second opening through which the longitudinal member extends.

BRIEF DESCRIPTION OF THE DRAWINGS

The foregoing and other features of the invention will become more apparent to those skilled in the art upon consideration of the following description taken in connection with the accompanying drawings, wherein.

DESCRIPTION OF A PREFERRED EMBODIMENT

Figure 1:
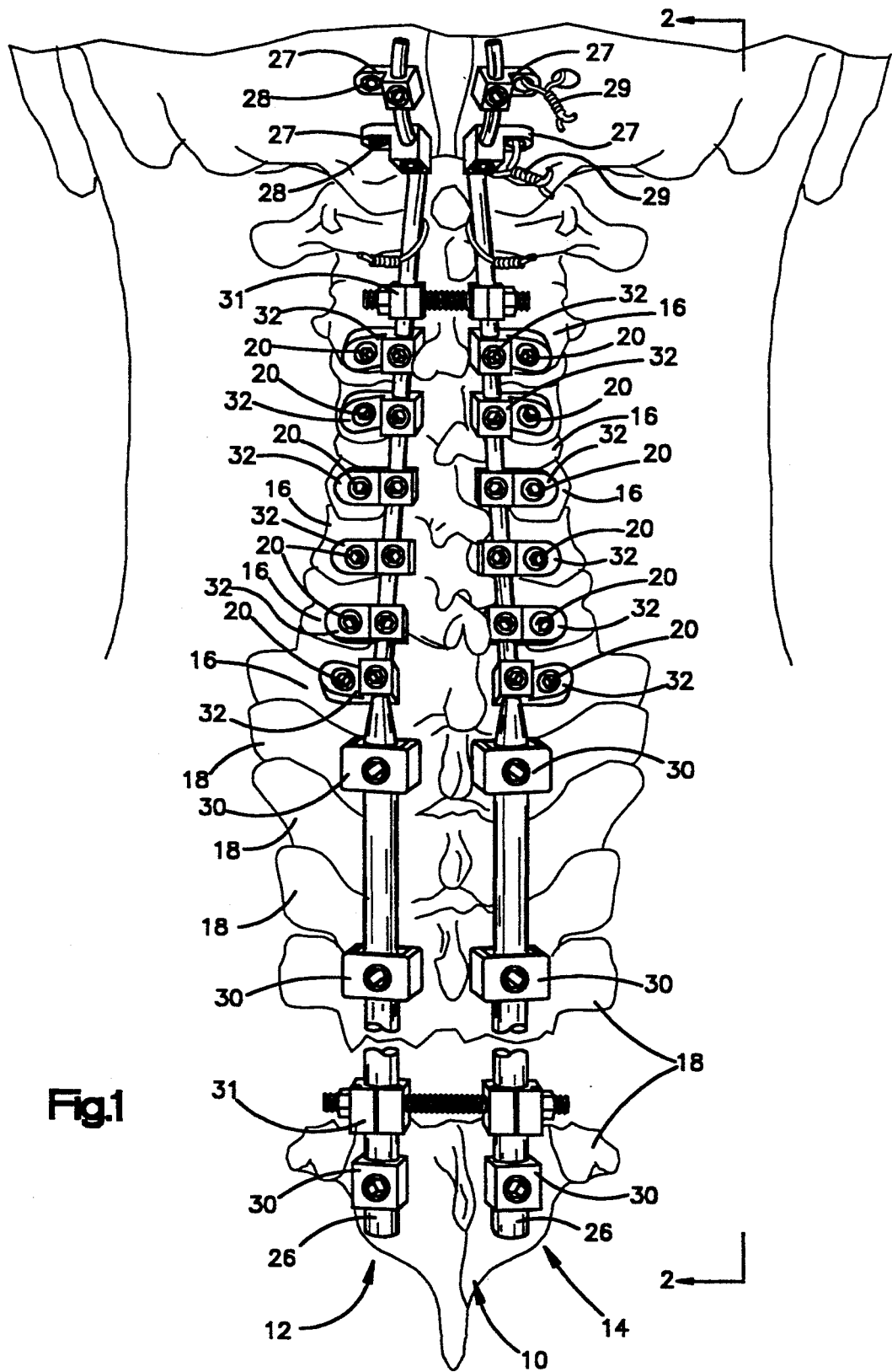
FIG. 1 is a dorsal view of a portion of a spinal column with retainer assemblies constructed and installed in accordance with the present invention to maintain a desired spatial relationship between vertebrae of the spinal column.
Figure 2:
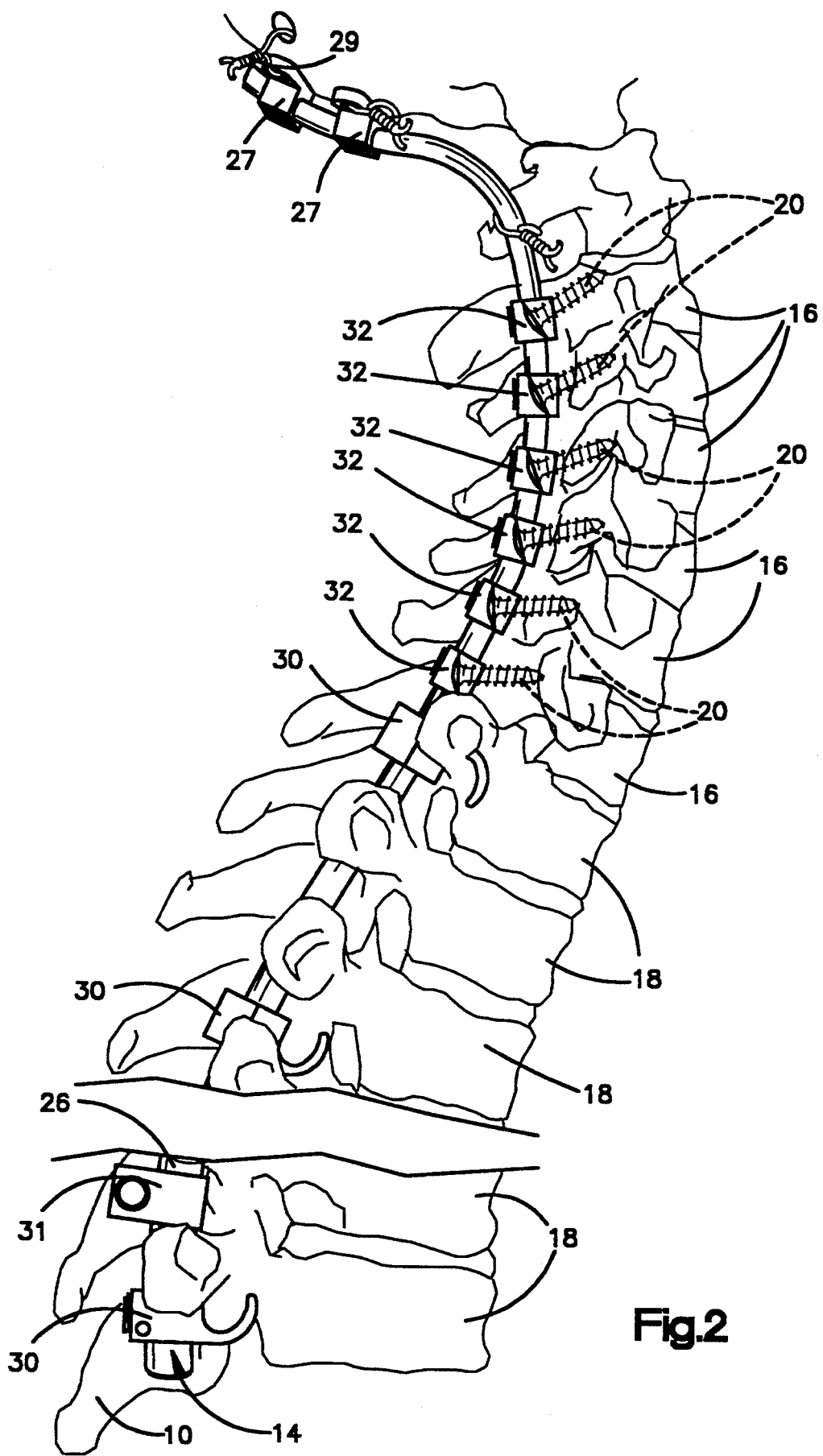
FIG. 2 is a sagittal view of the spinal column of FIG. 1, further illustrating the manner in which vertebrae of the spinal column are held in the desired spatial relationship.

A human spinal column 10 to which a pair of retainer assemblies 12 and 14 are connected is illustrated in FIGS. 1 and 2. The retainer assemblies 12 and 14 retain portions of the spinal column, that is cervical vertebrae 16 and thoracic vertebrae 18, in a desired spatial relationship relative to each other.

The retainer assemblies 12 and 14 have the same construction and include fasteners 20 located in the cervical vertebrae 16 of the spinal column 10 and made of a bio-compatible material, such as stainless steel. The fasteners 20 have threaded end portions which engage the vertebrae 16 to fixedly mount the fasteners in the vertebrae. Each of the retainer assemblies 12 and 14 also includes a longitudinal member such as the depicted cylindrical rod 26 which extends along the spinal column. The rod 26 is made of a bio-compatible material such as stainless steel. Each of the rods 26 has a length which is at least sufficient to enable the rod to span at least two of the cervical vertebrae 16. The rod 26 has a relatively large cross-sectional area located adjacent the thoracic vertebrae 18 of the spinal column 10 and a relatively small cross-sectional area located adjacent the cervical vertebrae 16 of the spinal column. The rods 26 are bent to conform to a desired curvature of the spinal column 10 in all or any of three possible anatomic planes.

The rods 26 are connected to the base of the skull by connectors 27. The rods 26 extend through openings in the connectors 27 and are fixed to the connectors 27 by set screws. The connectors 27 have openings for receiving a fastener such as a screw 28 or a wire 29 for connecting the connectors 27 to the skull.

Hooks 30, such as those disclosed in U.S. Pat. No. 5,024,213, interconnect the rods 26 to the thoracic vertebrae 18 of the spinal column 10 as is well known in the art. Although hooks 30 are shown connecting the rods 26 to the thoracic vertebrae 18, any known apparatus can be used to connect the rods to the thoracic vertebrae. Transverse connectors 31, such as those disclosed in U.S. Pat. No. 5,084,049, interconnect the retainer assemblies 12 and 14, also as is well known in the art.

Figure 3:
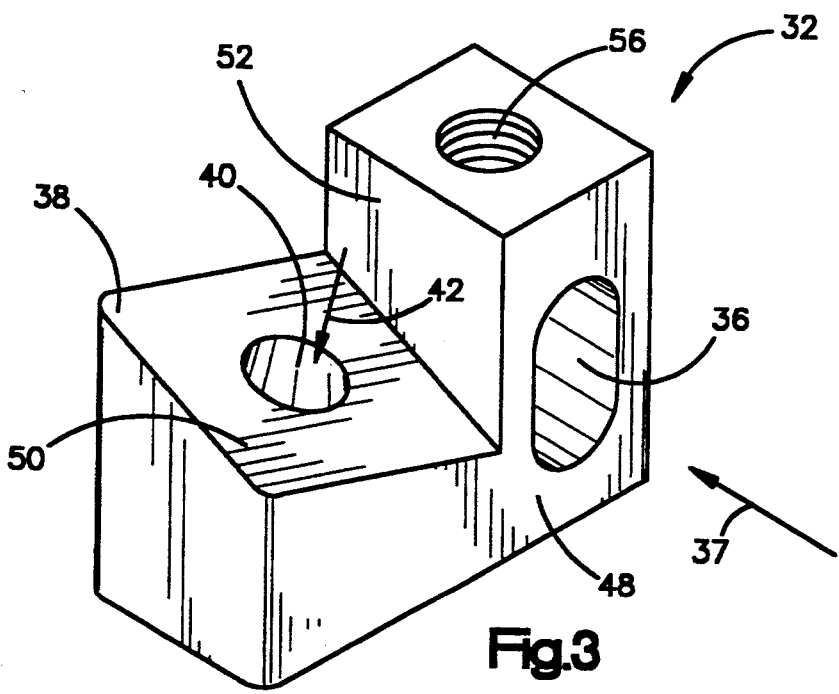
FIG. 3 is an enlarged pictorial illustration of a connector member of a first embodiment used in the left side retainer assembly of FIG. 1.

Connector members 32 of a first embodiment (FIGS. 3–5) interconnect the rods 26 and the fasteners 20 in the cervical region of the spinal column 10. Each of the connector members 32 is provided with a first opening 36 through which the rod 26 extends (FIG. 3). The first opening 36 extends through the connector member in a first direction indicated by arrow 37. Each of the connector members 32 has a mounting section 38 with a second tapered opening 40 through which the fastener 20 extends. The second opening 40 extends through the connector member in a second direction indicated by arrow 42.

The connector member 32 includes top and bottom surfaces 46 and 48 (FIG. 4) when connected to the spinal column 10. The longitudinal axis of the first opening 36, through which the rod 26 extends, is perpendicular to the top and bottom surfaces 46 and 48. The mounting section 38 has a side surface 50 that extends at an acute angle X, in FIG. 4, to the top and bottom surfaces 46 and 48. Therefore, the second direction 42, in which the second opening 40 extends, extends at an acute angle to a plane containing the top surface 46 and a plane containing the bottom surface 48. A surface 51 of the connector member 32 that engages the vertebra 16 when the connector member is connected to the vertebra may also extend at an angle to the top and bottom surfaces 46 and 48.

The connector member 32 also includes a surface 52 (FIGS. 3 and 5) that is parallel to the longitudinal axis of the first opening 36 through which the rod 26 extends. The side surface 50 of the mounting section 38 extends at an acute angle Y, in FIG. 5, to the surface 52. Therefore, the second direction 42 also extends at an acute angle to a plane containing the surface 52.

The connector member 32 has a threaded opening 56 for receiving a set screw (not shown). The set screw engages the rod 26 to push the rod against the side of the first opening 36. Thus, the set screw clamps the rod 26 to the connector member 32.

Figure 4:
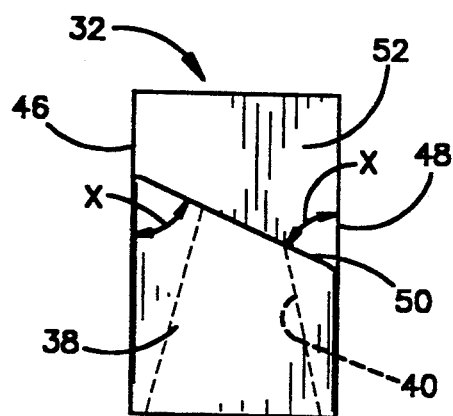
FIG. 4 is a lateral to medial view of the connector member of FIG. 3.
Figure 5:
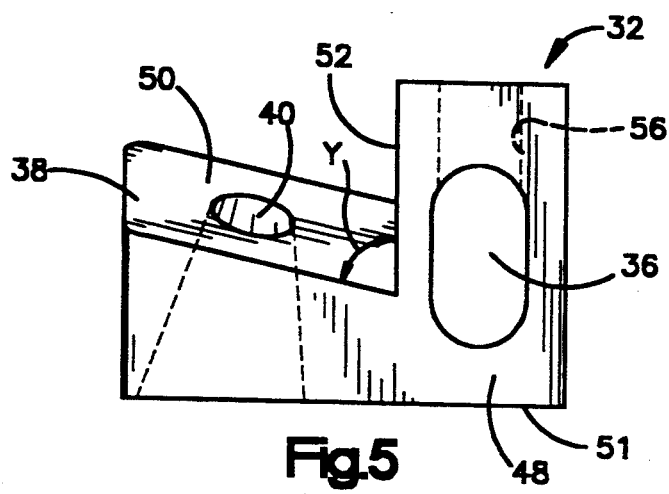
FIG. 5 is a caudad to cephalad view of the connector member of FIG. 3.
Figure 6:
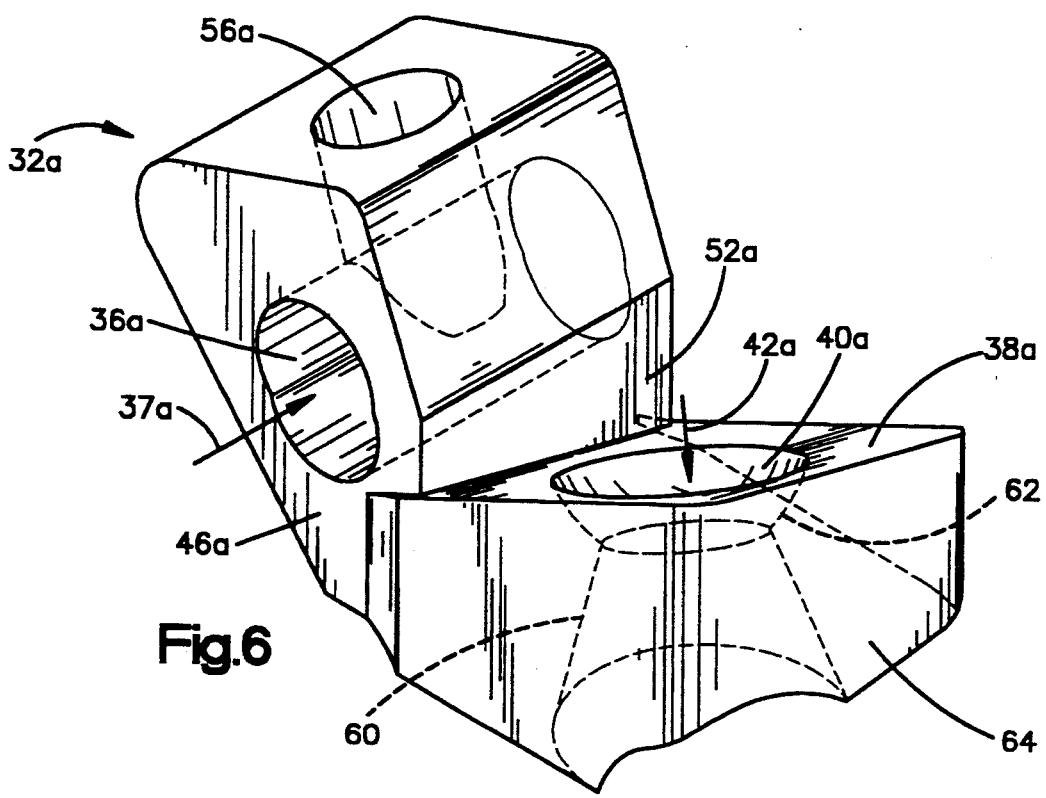
FIG. 6 is an enlarged pictorial illustration of a connector member of a second embodiment for a left side retainer assembly.
Figure 7:
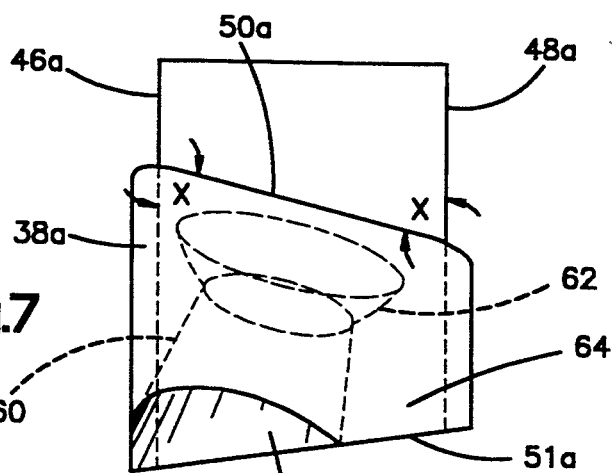
FIG. 7 is a lateral to medial view of the connector member of FIG. 6.
Figure 8:
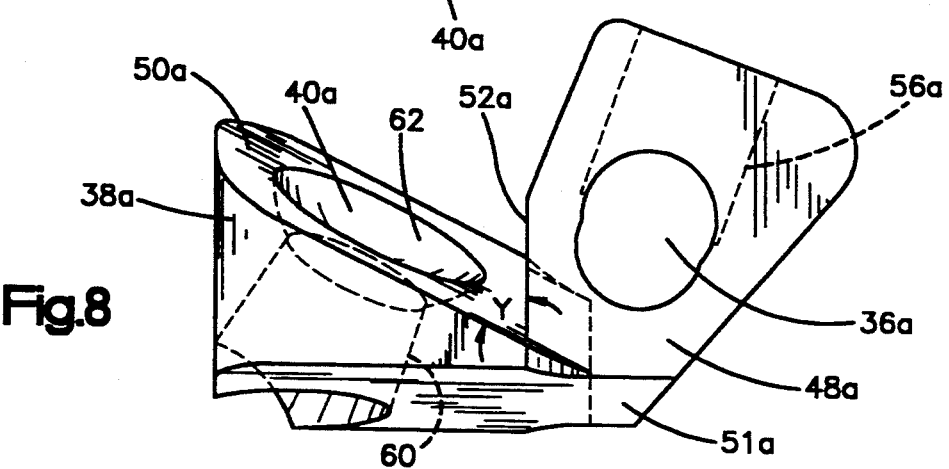
FIG. 8 is a caudad to cephalad view of the connector member of FIG. 6.

The embodiment of the invention illustrated in FIGS. 6–8 is generally similar to the embodiment of the invention illustrated in FIGS. 3–5, similar numerals will be utilized to designate similar components, the suffix letter "a" being associated with the numerals of FIGS. 6–8 to avoid confusion.

Connector member 32a is provided with a first opening 36a through which the rod 26 extends (FIG. 6). The first opening 36a extends through the connector member in a first direction indicated by arrow 37a. The connector member 32a has a mounting section 38a with a second opening 40a through which the fastener 20 extends. The second opening 40a extends through the connector member in a second direction indicated by the arrow 42a.

The opening 40a includes a tapered portion 60 and a spherical counter sink 62 for receiving a head of a fastener 20. The tapered portion 60 of the opening 40a extends through a side surface 64 and a surface 51a that engages the vertebra when the connector member 32a is connected to the vertebra.

The connector member 32a includes top and bottom surfaces 46a and 48a (FIG. 7) when connected to the spinal column 10. The longitudinal axis of the first opening 36a through which the rod 26 extends is perpendicular to the top and bottom surfaces 46a and 48a. The mounting section 38a has a side surface 50a that extends at an acute angle X, in FIG. 7, to the top and bottom surfaces 46a and 48a. Therefore, the second direction 42a, in which the second opening 40a extends, extends at an acute angle to a plane containing the top surface 46a and a plane containing the bottom surface 48a. The surface 51a also extends at an angle to the top and bottom surfaces 46a and 48a.

The connector member 32a also includes a surface 52a (FIGS. 6 and 8) that is parallel to the longitudinal axis of the first opening 36a through which the rod 26 extends. The side surface 50a of the mounting section 38a extends at an acute angle Y, in FIG. 8, to the surface 52a. Therefore, the second direction 42a also extends at an acute angle to a plane containing the surface 52a.

The connector member 32a has a threaded opening 56a for receiving a set screw (not shown). The set screw engages the rod 26 to push the rod against the side of the first opening 36a. Thus, the set screw clamps the rod 26 to the connector member 32a.

Although the connector members 32 and 32a are shown with threaded openings 56 and 56a for receiving a set screw, any known manner for clamping the rod 26 to the connector members may be used.

Although the connector members 32 and 32a have been shown with connectors 27, hooks 30 and transverse connectors 31, it is contemplated that they could be used alone in maintaining only the cervical vertebrae 16 in a desired spatial relationship or with other connectors such as clamps and sublaminar wires.

The configuration of the connector members 32 and 32a assure that the fasteners 20 extend into the cervical vertebrae 16 in a direction to provide a secure attachment of the rods 26 to the cervical vertebrae (FIG. 2). The angles that the side surfaces 50 and 50a of the mounting sections 38 and 38a make with the top surfaces 46 and 46a, the bottom surfaces 48 and 48a, and with the surfaces 52 and 52a depend on the configuration of the cervical vertebrae.

It should be apparent to those skilled in the art that certain modifications, changes and adaptations may be made in the present invention and that it is intended to cover all such modifications, changes and adaptations coming within the scope of the appended claims.

Having described the invention, the following is claimed:

1. An apparatus for use in retaining spinal elements in a desired spatial relationship, said apparatus comprising:
    a fastener for engaging a spinal element;
    a longitudinal member positionable along the spinal column; and
    a connector member for interconnecting said fastener and said longitudinal member, said connector member including surface means defining a first opening through which said longitudinal member extends, said connector member having a mounting section with surface means defining a second opening extending through a side surface of said mounting section and through which said fastener extends, the axis of the first opening through which said longitudinal member extends being perpendicular to top and bottom surfaces of said connector member, said side surface of said mounting section, through which said second opening extends, intersecting said top and bottom surfaces and extending at an acute angle to said top and bottom surfaces.

2. An apparatus as set forth in claim 1 wherein said side surface of said mounting section, through which said second opening extends, extends at an acute angle to a surface of said connector member perpendicular to said top and bottom surface and parallel to the longitudinal axis of the first opening through which said longitudinal member extends.

3. An apparatus for use in retaining spinal elements in a desired spatial relationship, said apparatus comprising a one-piece connector member for interconnecting a fastener for attaching said connector member to a vertebra of the spinal column and a longitudinal member, means for clamping said connector member to the fastener, and means for clamping said connector member to the longitudinal member, said connector member having first surface means defining a first opening extending through a first surface of said connector member in a first direction and through which the longitudinal member is extendable, said connector member having second surface means defining a second opening extending through said connector member in a second direction through which the fastener is extendable, said first direction extending perpendicular to said first surface of said connector member, said first surface of said connector member lying in a first plane, said second direction extending at an acute angle to the first plane.

4. An apparatus as set forth in claim 3 wherein said first direction extends parallel to a second surface of said connector member, said second surface of said connector member extending perpendicular to said first surface and lying in a second plane, said second direction extending at an acute angle to the second plane.

5. An apparatus as set forth in claim 3 wherein said connector member has a mounting section through which the second opening extends, said mounting section having a side surface, through which the second opening extends, extending at an acute angle to said first surface of said connector member.

6. An apparatus as set forth in claim 5 wherein said side surface of said mounting section, through which the second opening extends, extends at an acute angle to said second surface of said connector member.

* * * * *

UNITED STATES PATENT AND TRADEMARK OFFICE
CERTIFICATE OF CORRECTION

PATENT NO. : 5,403,314
DATED       : April 4, 1995
INVENTOR(S) : Bradford L. Currier, Karen E. Warden and James C. Bayley It is certified that error appears in the above-indentified patent and that said Letters Patent is hereby corrected as shown below:

Cover Page, Inventor section, change "Bardford" to --Bradford--.

Cover Page, Inventor section, after "Minn." insert --, Karen E. Warden, Cleveland Ohio and James C. Bayley, Chestnut Hill, Mass.--.

Signed and Sealed this

Twenty-second Day of August, 1995

Attest:

BRUCE LEHMAN

Attesting Officer       Commissioner of Patents and Trademarks

UNITED STATES PATENT AND TRADEMARK OFFICE
CERTIFICATE OF CORRECTION

PATENT NO. : 5,403,314
DATED : April 4, 1995
INVENTOR(S) : Bradford L. Currier, et. al.

It is certified that error appears in the above-indentified patent and that said Letters Patent is hereby corrected as shown below:

Title page, item [73], Assignee: after "Ohio" insert-- and Mayo Foundation for Medical Education and Research, Rochester, Minn.--.

Signed and Sealed this

Twenty-fourth Day of October, 1995

Attest:

BRUCE LEHMAN

*Attesting Officer*     *Commissioner of Patents and Trademarks*